US009962238B2

(12) United States Patent
Boltunov et al.

(10) Patent No.: US 9,962,238 B2
(45) Date of Patent: May 8, 2018

(54) DIGITAL DENTAL MODELING

(71) Applicant: Align Technology, Inc., San Jose, CA (US)

(72) Inventors: Anatoliy Boltunov, Moscow (RU); Yury Brailov, Moscow (RU); Fedor Chelnokov, Khimi Town (RU); Roman Roschin, Moscow (RU); David Mason, Morgan Hill, CA (US)

(73) Assignee: Align Technology, Inc., San Jose, CA (US)

( * ) Notice: Subject to any disclaimer, the term of this patent is extended or adjusted under 35 U.S.C. 154(b) by 70 days.

(21) Appl. No.: 15/006,573

(22) Filed: Jan. 26, 2016

(65) Prior Publication Data

US 2016/0135927 A1 May 19, 2016

Related U.S. Application Data

(62) Division of application No. 14/553,556, filed on Nov. 25, 2014, now Pat. No. 9,256,710, which is a division (Continued)

(51) Int. Cl.
*A61C 7/00* (2006.01)
*A61C 7/08* (2006.01)
(Continued)

(52) U.S. Cl.
CPC ............... *A61C 7/002* (2013.01); *A61C 7/08* (2013.01); *A61C 9/004* (2013.01); *G06F 19/12* (2013.01);
(Continued)

(58) Field of Classification Search
None
See application file for complete search history.

(56) References Cited

U.S. PATENT DOCUMENTS

| 4,123,768 A | 10/1978 | Kilshaw et al. |
| 4,825,393 A | 4/1989 | Nishiya |

(Continued)

FOREIGN PATENT DOCUMENTS

| EP | 1549244 A1 | 7/2005 |
| EP | 1549244 B1 | 7/2005 |

(Continued)

OTHER PUBLICATIONS

Hecker et al., "Physics, Part 4: The Third Dimension," Game Developer, Jun. 1997, pp. 15-26, http:www.d6.com/users/checker.

(Continued)

*Primary Examiner* — Ke Xiao
*Assistant Examiner* — Jed-Justin Imperial
(74) *Attorney, Agent, or Firm* — Brooks, Cameron & Huebsch, PLLC

(57) ABSTRACT

Embodiments are provided for digital dental modeling. One method embodiment includes receiving a three-dimensional data set including a first jaw and a second jaw of a three-dimensional digital dental model and receiving a two-dimensional data set corresponding to at least a portion of the first jaw and the second jaw. The method includes mapping two-dimensional data of the two-dimensional data set to the three-dimensional digital dental model by transforming a coordinate system of the two-dimensional data to a coordinate system of the three-dimensional data set. The method includes positioning the first jaw with respect to the second jaw based on the two-dimensional data mapped to the three-dimensional data set. The method includes using at least a portion of the two-dimensional data mapped to the three-dimensional data set as a target of movement of the first jaw with respect to the second jaw in the three-dimensional digital dental model.

20 Claims, 11 Drawing Sheets

Related U.S. Application Data of application No. 12/583,479, filed on Aug. 21, 2009, now Pat. No. 8,896,592.

(51) Int. Cl.

| | | |
|---|---|---|
| *G06T 19/20* | (2011.01) | |
| *A61C 9/00* | (2006.01) | |
| *G06F 19/12* | (2011.01) | |
| *G06T 17/00* | (2006.01) | |
| *G06T 7/30* | (2017.01) | |
| *G06T 7/70* | (2017.01) | |

(52) U.S. Cl.
CPC ............... *G06T 7/30* (2017.01); *G06T 7/70* (2017.01); *G06T 17/00* (2013.01); *G06T 19/20* (2013.01); *G06T 2219/2004* (2013.01)

(56) References Cited

U.S. PATENT DOCUMENTS

| | | | |
|---|---|---|---|
| 4,859,181 A * | 8/1989 | Neumeyer | A61B 5/1114 433/69 |
| 5,905,658 A | 5/1999 | Baba | |
| 6,120,290 A | 9/2000 | Fukushima et al. | |
| 6,512,994 B1 | 1/2003 | Sachdeva | |
| 6,979,196 B2 | 12/2005 | Nikolskiy et al. | |
| 7,220,124 B2 | 5/2007 | Taub et al. | |
| 7,234,937 B2 | 6/2007 | Sachdeva et al. | |
| 7,880,751 B2 | 2/2011 | Kuo et al. | |
| 7,942,671 B2 | 5/2011 | Taub et al. | |
| 8,454,364 B2 | 6/2013 | Taub et al. | |
| 2002/0094509 A1 | 7/2002 | Durbin et al. | |
| 2002/0150859 A1 | 10/2002 | Imgrund et al. | |
| 2004/0224286 A1 | 11/2004 | Kaza | |
| 2005/0136371 A1 | 6/2005 | Abolfathi | |
| 2005/0191593 A1 * | 9/2005 | Knopp | A61C 7/00 433/24 |
| 2007/0207437 A1 | 9/2007 | Sachdeva et al. | |
| 2007/0207441 A1 | 9/2007 | Lauren | |
| 2008/0038684 A1 | 2/2008 | Keating et al. | |
| 2008/0057478 A1 | 3/2008 | Choi | |
| 2011/0183294 A1 | 7/2011 | Taub et al. | |
| 2013/0246014 A1 | 9/2013 | Taub et al. | |

FOREIGN PATENT DOCUMENTS

| | | |
|---|---|---|
| EP | 2465464 A2 | 6/2012 |
| JP | 2006501010 A | 1/2006 |
| WO | 2004/030565 A1 | 4/2004 |
| WO | 2006/065955 A2 | 6/2006 |
| WO | 2006/085851 A1 | 8/2006 |

OTHER PUBLICATIONS

Horn, "Closed-form solution of absolute . . . ," Journal of Optical Society of America, vol. 4, 1987, pp. 629-642.
University of Nevada. "Geometric Camera Parameters". http://www.cse.unr.edu/~bebis/CS791E/Notes/CameraParameters.pdf, Accessed Aug. 21, 2009 (9 pgs).
Weingarten, J.W., et al. "Probabilistic Plane Fitting in 3D and an Application . . . ". IEEE Int'l Conference on Robotics and Automation Proceedings, vol. 1, pp. 927-932 (2004).
International Search Report corresponding to International Patent Application PCT/IB2010/002063, dated May 7 2012.
Summons to Attend Oral Proceedings from related European Patent Application No. 10754366.2, dated Jul. 4, 2017, 9 pages.

* cited by examiner

DIGITAL DENTAL MODELING

RELATED APPLICATIONS

This application is a divisional of U.S. application Ser. No. 14/553,556, filed Nov. 25, 2014, which is a divisional of U.S. application Ser. No. 12/583,479, filed Aug. 21, 2009, which issued as U.S. Pat. No. 8,896,592 on Nov. 25, 2014, the entire contents of which are hereby incorporated by reference.

BACKGROUND

The present disclosure is related generally to the field of dental treatment. More particularly, the present disclosure is related to methods, devices, and systems for bite setting digital dental models.

Many dental treatments involve repositioning misaligned teeth and changing bite configurations for improved cosmetic appearance and dental function. Orthodontic repositioning can be accomplished, for example, by applying controlled forces to one or more teeth over a period of time.

An example of orthodontic repositioning that can occur can be through a dental process that uses positioning appliances for realigning teeth. Such appliances may utilize a thin shell of material having resilient properties, referred to as an "aligner" that generally conforms to a patient's teeth but is slightly out of alignment with the initial tooth configuration.

Placement of such an appliance over the teeth can provide controlled forces in specific locations to gradually move the teeth into a new configuration. Repetition of this process with successive appliances in progressive configurations can move the teeth through a series of intermediate arrangements to a final desired arrangement.

Such systems typically utilize materials that are light weight and/or transparent to provide as a set of appliances that can be used serially such that as the teeth move, a new appliance can be implemented to further move the teeth.

With computer-aided teeth treatment systems, an initial digital data set (IDDS) representing an initial tooth arrangement may be obtained. The IDDS may be obtained in a variety of ways. For example, the patient's teeth may be scanned or imaged using X-rays, three-dimensional X-rays, computer-aided tomographic images or data sets, magnetic resonance images, etc.

A cast (e.g., a plaster cast and/or mold) of the patient's teeth may be scanned using a laser scanner or other range acquisition system to produce the IDDS. The data set produced by the range acquisition system may be converted to other formats to be compatible with the software which is used for manipulating images within the data set, as described herein.

After scanning, computer models of teeth on an upper jaw and a lower jaw may be generated. However, these models may not be aligned with respect to each other. Thus, a bite setting operation may be performed to align the digital dental model including the upper and lower jaws.

DETAILED DESCRIPTION

Embodiments are provided for digital dental modeling. One method embodiment includes receiving a three-dimensional data set including a first jaw and a second jaw of a three-dimensional digital dental model and receiving a two-dimensional data set corresponding to at least a portion of the first jaw and the second jaw. The method includes mapping two-dimensional data of the two-dimensional data set to the three-dimensional digital dental model by transforming a coordinate system of the two-dimensional data to a coordinate system of the three-dimensional data set. The method includes positioning the first jaw with respect to the second jaw based on the two-dimensional data mapped to the three-dimensional data set. The method includes using at least a portion of the two-dimensional data mapped to the three-dimensional data set as a target of movement of the first jaw with respect to the second jaw in the three-dimensional digital dental model.

Some method embodiments can include receiving a three-dimensional data set including an upper jaw and a lower jaw of a three-dimensional digital dental model. Such embodiments can include receiving a plurality of two-dimensional data sets each corresponding to at least a portion of the upper jaw and the lower jaw. Some embodiments can include mapping two-dimensional data of the plurality of two-dimensional data sets to the three-dimensional digital dental model by transforming a coordinate system of the two-dimensional data to a coordinate system of the three-dimensional data set. One or more embodiments can include simulating anatomical movement of the lower jaw with respect to the upper jaw based on the two-dimensional data mapped to the three-dimensional data set in the three-dimensional digital dental model.

One or more system embodiments can include a three-dimensional digital dental model including a first jaw and a second jaw. Such systems can include a two-dimensional image of a patient's teeth corresponding to the teeth of the three-dimensional digital dental model. The systems can include a correlation module configured to correlate the two-dimensional image with the three-dimensional digital dental model.

Figure 1:
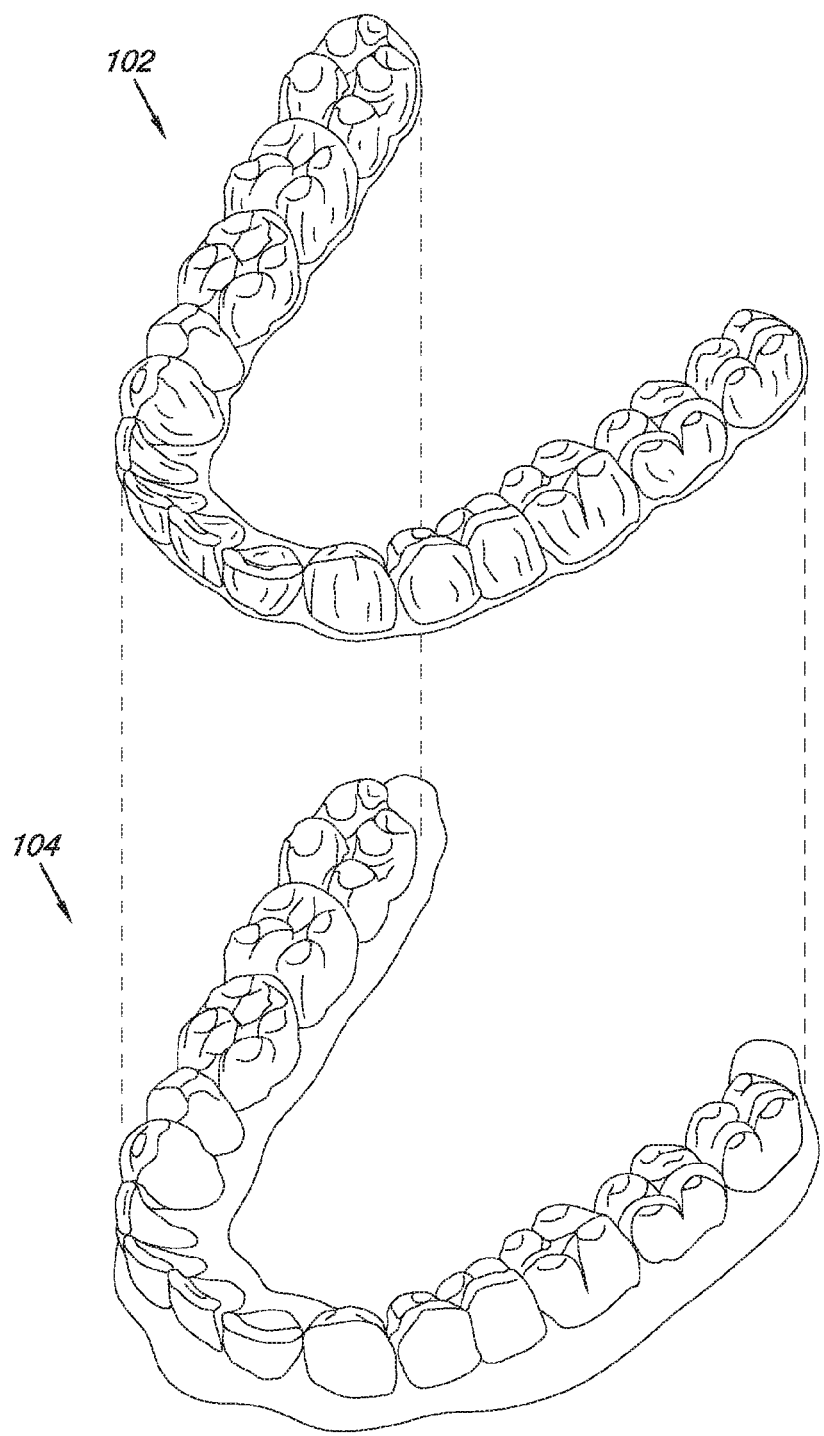
FIG. 1 illustrates a dental position adjustment appliance being applied to a set of teeth according to one or more embodiments of the present disclosure.
Figure 2:
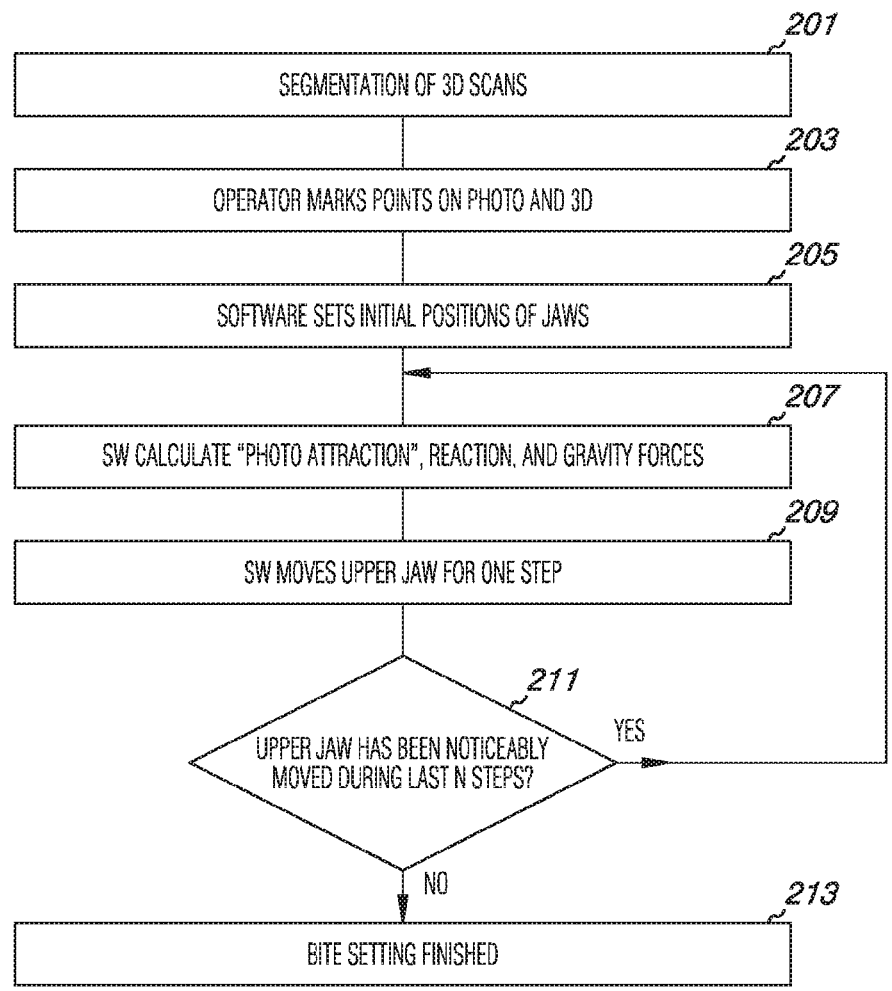
FIGS. 2-5 are flow charts illustrating methods for digital dental modeling according to one or more embodiments of the present disclosure.

FIG. 1 illustrates a dental position adjustment appliance being applied to a set of teeth according to one or more embodiments of the present disclosure. Appliances according to the present disclosure can include, in some embodiments, a plurality of incremental dental position adjustment appliances. The appliances, such as appliance 102 illustrated in FIG. 1, can be utilized to affect incremental repositioning of individual teeth in the jaw, among other suitable uses.

Appliances can include any positioners, retainers, and/or other removable appliances for finishing and maintaining teeth positioning in connection with a dental treatment. These appliances may be utilized by the treatment professional in performing a treatment plan. For example, a treatment plan can include the use of a set of appliances, created according to models described herein.

An appliance (e.g., appliance 102 in FIG. 1) can, for example, be fabricated from a polymeric shell, and/or formed from other material, having a cavity shaped to receive and apply force to reposition one or more teeth from one teeth arrangement to a successive teeth arrangement. The shell may be designed to fit over a number of, or in many instances all, teeth 104 present in the upper and/or lower jaw.

FIGS. 2-5 are flow charts illustrating methods for digital dental modeling according to one or more embodiments of the present disclosure. At 201 in FIG. 2, three-dimensional (3D) scans of physical dental molds of a patient's jaws can be segmented into a number of teeth. That is, each tooth can be modeled individually. For example, each tooth can be modeled as a 3D mesh space volume having a particular density. In some embodiments, all teeth can be modeled with the same density.

At 203, an operator (e.g., a dental professional) can mark points on a photograph of a patient's jaws in a bite configuration and on the digital 3D model of the patient's jaws. The points marked on the digital model of the patient's jaws can correspond to the points marked on the photograph (e.g., both sets of points can have a 1:1 correspondence such that each point marked on the photograph has a corresponding point marked on the digital dental model). As described herein, using close-range photography can aid in the accuracy of the correspondence between points marked on the digital dental model and points marked on the photograph.

At 205, software can set initial positions of the digital model of the patient's jaws. When the scans of the physical dental molds are segmented into a number of teeth, a relational correspondence between teeth in the upper jaw and lower jaw of the digital dental model can be determined. For example, a general relational (e.g., positional) correspondence between a right upper incisor and a right lower incisor can aid in setting an initial position for the dental (e.g., digital) model of the patient's jaws. In some embodiments, an initial position can be set according to a class of occlusion associated with the patient (e.g., normal, overbite, or underbite).

At 207, software can calculate a number of forces including photo attraction forces, reaction forces, and an axial force (e.g., gravity). Photo attraction forces can include forces applied at a number of points marked on the 3D digital dental model corresponding to a number of points marked on a 2D image of a patent's jaws in a bite configuration. The photo attraction forces can be simulated in a direction parallel to a plane fit to the number of points marked on the digital dental model and toward a number of points mapped to the plane from the number of points marked on the two-dimensional image. Such forces can assist the bite setting operation in converging on a correct and/or accurate solution.

Reaction forces can include forces arising from a simulated collision between a fixed jaw of the digital dental model and a non-fixed jaw of the digital dental model, or between two non-fixed jaws of the digital dental model. During simulation of movement, if the two jaws have not come into contact from their initial positions, then there would be zero reaction force acting on the digital dental model. As used herein, a fixed jaw of the digital dental model is a jaw that has one or more degrees of freedom constrained within the model (e.g., all six degrees of freedom can be constrained for the fixed jaw).

An axial force can be simulated along an axial direction between the two jaws of the digital dental model. For example, the axial force can be applied along an axis between the center of mass of the upper jaw and a center of mass of the lower jaw. In some embodiments, the axial force can be simulated as gravity.

At 209, software can move a first jaw (e.g., the upper jaw) for one step. The first jaw can move in response to the number of forces calculated at 207 being applied to the first jaw. In some embodiments, simulation of movement can be divided into a number of steps (e.g., discrete time steps). Such embodiments can allow for recalculation of forces between movement elements (e.g., time steps).

At 211, if the upper jaw has noticeably moved during the last N steps, the method can return to 207, where the number of forces can be recalculated. In such instances, movement of the first jaw can be simulated in response to the recalculated forces. At 211, if the upper jaw has not noticeably moved during the last N steps, the bite setting can be finished at 213. The position of the upper and lower jaws at this point can be reported as the bite set.

Although the upper jaw of the digital dental model may be described generally as the non-fixed jaw while the lower jaw of the digital dental model may be described as the fixed jaw, embodiments are not so limited. For example, in some embodiments, the upper jaw may be fixed while the lower jaw is non-fixed. In various embodiments, both jaws can be non-fixed.

Figure 3:
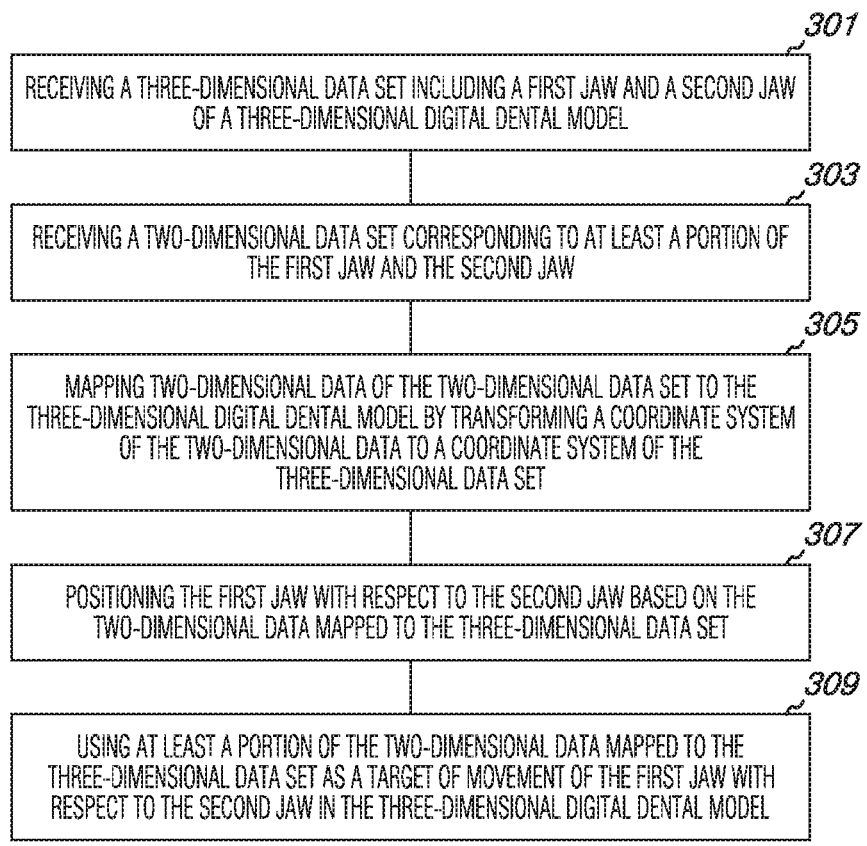

FIG. 3 is a flow chart illustrating a method for digital dental modeling according to one or more embodiments of the present disclosure. At 301, the method can include receiving a three-dimensional data set including a first jaw and a second jaw of a three-dimensional digital dental model. At 303, the method can include receiving a two-dimensional data set corresponding to at least a portion of the first jaw and the second jaw.

At 305, the method can include mapping two-dimensional data of the two-dimensional data set to the three-dimensional digital dental model by transforming a coordinate system of the two-dimensional data to a coordinate system of the three-dimensional data set. The two-dimensional data set, as used herein, refers to a collection of individual two-dimensional data points.

At 307, the method can include positioning the first jaw with respect to the second jaw based on the two-dimensional data mapped to the three-dimensional data set. For example, such positioning can set initial relative positions of the first and the second jaw of the three-dimensional digital dental model.

At 309, the method can include using at least a portion of the two-dimensional data mapped to the three-dimensional data set as a target of movement of the first jaw with respect to the second jaw in the three-dimensional digital dental model. Using two-dimensional data mapped to the three-dimensional data set can help provide a more accurate bite set than is provided according to some previous approaches.

Figure 4:
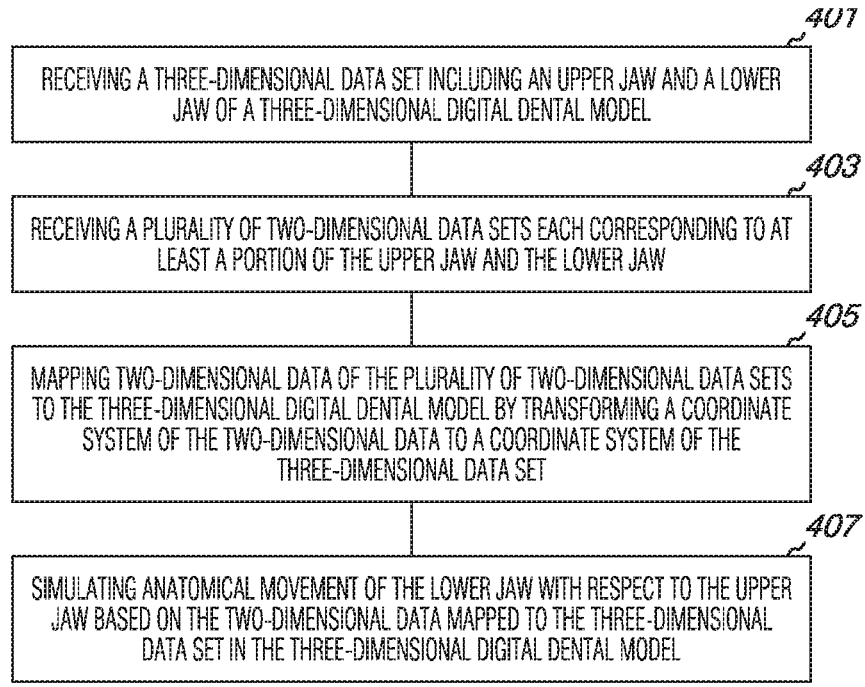

FIG. 4 is a flow chart illustrating a method for digital dental modeling according to one or more embodiments of the present disclosure. At 401, the method can include receiving a three-dimensional data set including an upper jaw and a lower jaw of a three-dimensional digital dental model. In one or more embodiments, data corresponding to the upper jaw and the lower jaw of the three-dimensional data set can be acquired separately.

At 403, the method can include receiving a plurality of two-dimensional data sets each corresponding to at least a portion of the upper jaw and the lower jaw. For example, each of the plurality of two-dimensional data sets can be associated with a respective photograph. In some embodiments, each respective photograph can be a photograph of a patient's jaw in one of a number of positions between opened and closed, inclusively.

At 405, the method can include mapping two-dimensional data of the plurality of two-dimensional data sets to the three-dimensional digital dental model by transforming a coordinate system of the two-dimensional data to a coordinate system of the three-dimensional data set. For example, data associated with one or more photographs of a patient's jaws can be mapped onto a digital dental model of the patient's jaws.

At 407, the method can include simulating anatomical movement of the lower jaw with respect to the upper jaw based on the two-dimensional data mapped to the three-dimensional data set in the three-dimensional digital dental model. For example, such simulated anatomical movement can represent an opening and/or closing of a patient's jaws.

Figure 5:
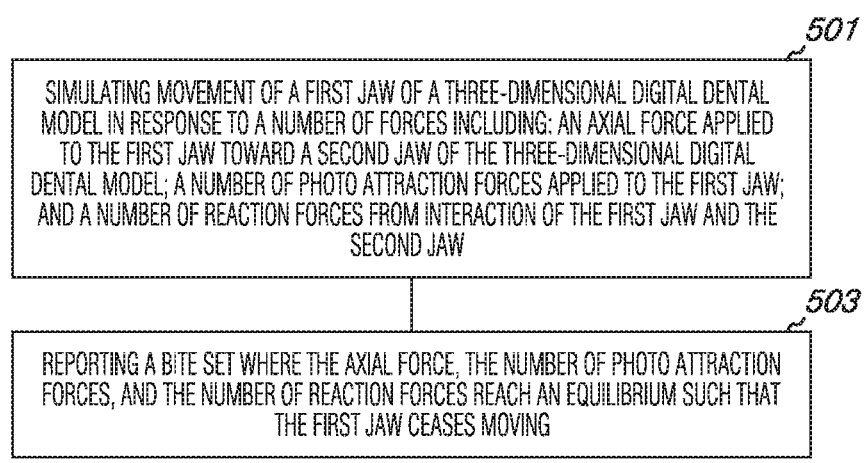

FIG. 5 is a flow chart illustrating a method for digital dental modeling according to one or more embodiments of the present disclosure. At 501, the method can include simulating movement of a first jaw of a three-dimensional digital dental model in response to a number of forces including: an axial force applied to the first jaw toward a second jaw of the three-dimensional digital dental model, a number of photo attraction forces applied to the first jaw, and a number of reaction forces from interaction of the first jaw and the second jaw.

At 503, the method can include reporting a bite set where the axial force, the number of photo attraction forces, and the number of reaction forces reach an equilibrium such that the first jaw ceases moving. When the forces acting on the three-dimensional digital dental model reach an equilibrium, the simulation can transition from dynamic to static. That is, the non-fixed jaw can cease moving in the simulation and a stable bit set can be reached.

The discussion of FIGS. 6-9 includes reference to a number of points. For clarity, a brief description of the various points is in order. Points denoted "x" (lower case) represent points marked on a two-dimensional (2D) image (e.g., a photograph) of a patient's teeth. Points denoted "x" can have a 2D coordinate system (e.g., because the x points are associated with a 2D image).

Points denoted "X" (upper case) represent points marked on a 3D digital dental model associated with the patient's teeth that correspond to x (lower case) points, as described herein. For example, a particular X point marked on the 3D digital dental model can correspond to a particular x point marked on the 2D image of the patient's teeth (e.g., the particular X point and the particular x point can be marked in essentially the same position on the patient's teeth). X (upper case) points can have a 3D coordinate system (e.g., because the X points are associated with a 3D model).

Points denoted "Y" represent X points fit to a common plane p (e.g., projected onto plane p), as described herein. That is, X points marked on the 3D digital dental model may not inherently fit a common plane because they are marked in a 3D coordinate system. However, according to one or more embodiments of the present disclosure, X points can be projected to a common plane "p," and after which are denoted as Y points (e.g., a change in 3D coordinates for a particular X point may occur when the particular X point is projected to the plane p).

Points denoted "$G^{-1}(x)$" represent 2D x points that are mapped to the 3D digital dental model. That is, a 2D coordinate system associated with the x points can be transformed to a 3D coordinate system associated with the 3D digital dental model. As such, the x points can be "put on" the digital dental model and denoted as "$G^{-1}(x)$ points." Details associated with these various points are included with the discussion of FIGS. 6-9 below.

Figure 6:
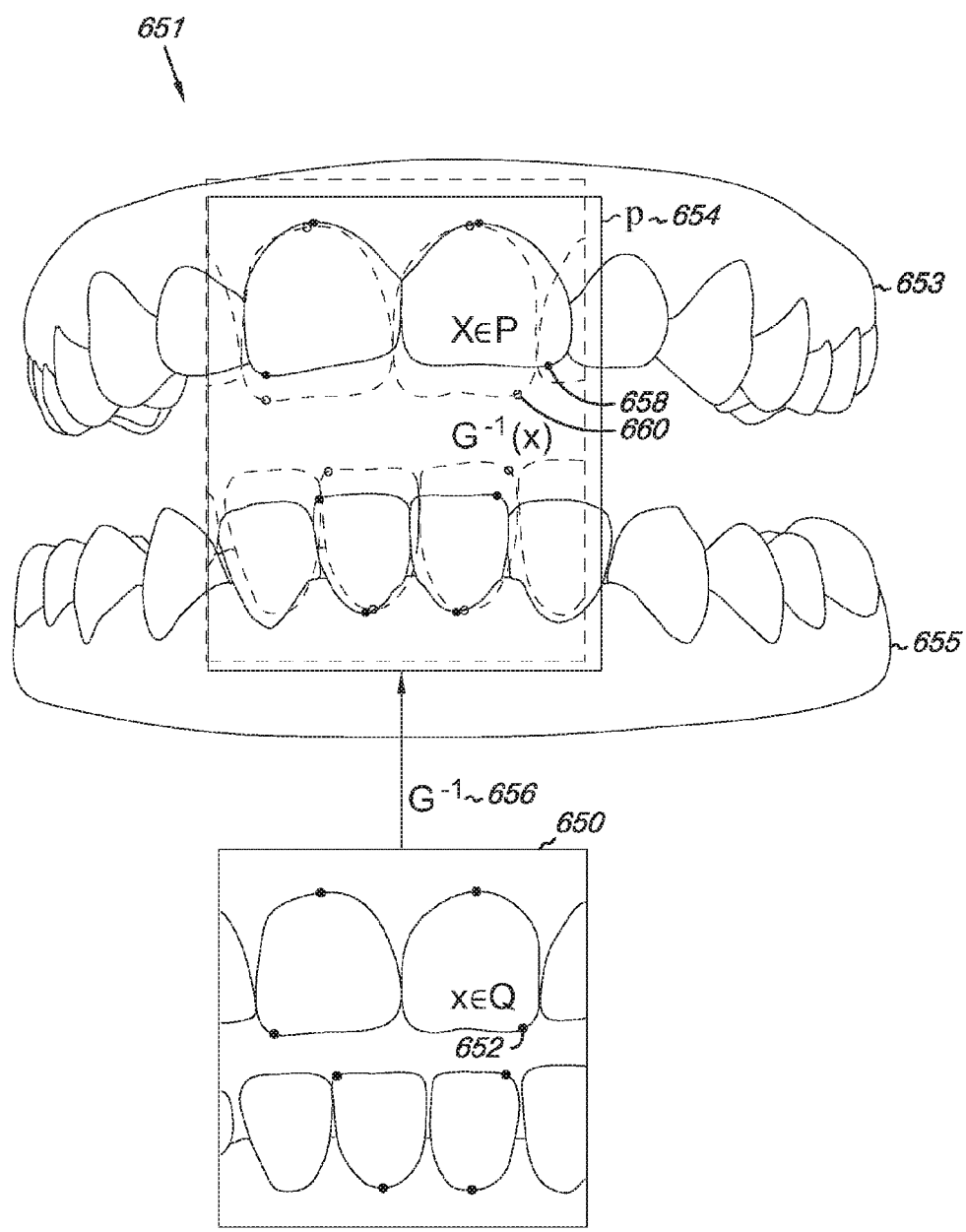
FIG. 6 illustrates a photograph of a portion of a patient's jaws and a digital dental model corresponding to the patient's jaws according to one or more embodiments of the present disclosure.

FIG. 6 illustrates a photograph of a portion of a patient's jaws and a digital dental model corresponding to the patient's jaws according to one or more embodiments of the present disclosure. The 2D image (e.g., photograph) 650 depicts a number of teeth from a patient's upper jaw (e.g., upper arch) and lower jaw (e.g., lower arch) in a bite configuration. That is, the photograph can be taken of the patient's teeth while the patient is biting. Such embodiments can provide a reference for an accurate bite alignment of a digital dental model 651 of the patient's jaws.

A 2D data set can include a portion of data received from a 2D imaging device (e.g., a camera). The 2D data set can include a portion of data received from a GUI displaying a 2D image, where the portion of data received from the GUI includes at least three points marked on the 2D image.

A 3D data set (e.g., an IDDS) can include a portion of data received from a scan of a patient's teeth or a scan of a physical model (e.g., mold) of the patient's teeth. The 3D data set can include a portion of data received from a GUI displaying a 3D digital dental model, where the portion of data received from the GUI includes at least three points marked on a jaw of the 3D digital dental model.

As described herein, data comprising the upper jaw 653 and the lower jaw 655 may be obtained independently of each other and/or without information about relative positions of the upper jaw 653 and the lower jaw 655 in a bite configuration. Mapping information about the patient's jaws in a bite configuration (e.g., from a photograph thereof) can aid in bite setting the 3D digital dental model 651. That is, such information can aid in accurately positioning the upper jaw 653 and the lower jaw 655 in a bite configuration.

One or more embodiments can include acquiring a 2D image and data comprising the 3D digital dental model at a same stage of patient treatment. Some embodiments can include acquiring the 2D image at a later stage of patient treatment than a stage during which data comprising the 3D digital dental mode is acquired. That is, photographs of a patient's teeth can be taken at a later stage of treatment to be used to update the digital dental model without the time and expense of reacquiring the 3D data.

In some embodiments, the photograph 650 can be a close-range photograph. A close-range photograph may have a shallow depth of sharply reproduced space (e.g., depth of field). That is, a close-range photograph may only be in focus for a narrow range of distances from the lens of the camera (e.g., a few millimeters). Accordingly, a number of points on a close-range photograph image that are in focus can be approximated as being within a same plane (e.g., to within an error corresponding to the depth of field associated with the particular image).

According to one or more embodiments of the present disclosure, the patient's upper and lower jaw can be two-dimensionally imaged (e.g., photographed) with a 2D imaging device (e.g., a camera) without applying physical targets to the patient. Such embodiments can provide a number of advantages over some previous approaches which required the use of targets fixed to the subject of the photograph in order to later correlate 2D and 3D data.

According to one or more embodiments of the present disclosure, an operator (e.g., a dental professional) can mark a number of first points (e.g., x points) on the photograph 650. In some embodiments, the x points can be marked on sharp singularities (e.g., points that are in focus on the image). In one or more embodiments, x points can be marked on dental reference points (e.g., cusp tips). The photograph 650 is shown marked with a number of x points (e.g., point 652). The number of points marked on the photograph can be represented by the set Q, where x represents a member (e.g., point 652) of the set Q (e.g., x∈Q).

In various embodiments, the operator can mark a number of second points (e.g., X points) on the 3D digital dental model 651 that correspond to the x points marked on the photograph. The number of points marked on the digital dental model can be represented by the set P, where X represents a member (e.g., point 658) of the set P (e.g., X∈P).

The operator can mark corresponding X points on the digital dental model by reference to a printed photograph, a scanned image of a printed photograph on a display, or a copy of a digital image on a display, among other types of photograph images having marked x points. For example, the operator can mark point 652 on photograph 650 and then mark point 658 on the digital dental model 651. That is, the operator can mark an x point at a particular location on the patient's teeth on the photograph, and then mark a corresponding X point at the same particular location on the patient's teeth on the digital dental model.

The operator can mark x points on a printed photograph with a writing utensil and/or on a digital image of a photograph on a display using an input to a computing device (e.g., through a graphical user interface (GUI) associated with the computing device). Likewise, the operator can mark X points on a digital dental model using an input (e.g., a mouse, stylus, touch screen, etc.) to a computing device having a display of an image of the digital dental model. In one or more embodiments, the number of x points marked on the photograph can be equal to the number of X points marked on the digital dental model (e.g., both the photograph and the digital dental model can have a number of points equal to k marked thereon).

A coordinate system for the photograph can be determined by a computing device according to the number of points marked on the photograph (e.g., on a digital photograph or on a scanned image of a physical photograph). Likewise, an operator can mark a number of points on a physical photograph and determine a coordinate system independently of the computing device (e.g., using a ruler or other measuring device). In such embodiments, the operator can enter the coordinate information corresponding to the points marked on the photograph into a computing device.

In various embodiments, a rough approximation of a bite for the digital dental model may be provided (e.g., an initial position of the upper jaw 653 and the lower jaw 655 of the digital dental model 651 with respect to each other). As data comprising the upper jaw 653 may be obtained separately from data comprising the lower jaw 655 (e.g., from a scan of a patient's upper bite mold and a scan of a patient's lower bite mold), some initial positioning can help correlate otherwise unrelated data. With initial positioning, the set of points P marked on the upper jaw 653 and the lower jaw 655 of the digital dental model 651 can have a common 3D coordinate system.

To facilitate mapping of the x points to the 3D digital dental model 651, the X points can be projected to a plane as described herein. A plane p can be fit to the set of points P. For example, a plane p can be fit to set P by a least-square fit method.

Plane p can have an orthogonal projection π. The set of X points P on the digital dental model can be projected on plane p and denoted as third points (e.g., Y points). The Y points can have a defined coordinate system on plane p:

$$Y_i = (Y_{i1}, Y_{i2}), i=1, \ldots, k \qquad (1)$$

The deviation of the set P from the plane p can be negligible compared to the distance of a point X in set Q to the camera. For example, non-planarity of cloud P (e.g., the 3D set of points P) can be about 3 mm for a 500×300 resolution (e.g., approximately 0.15 mm per pixel) photograph taken of an approximately 10 mm tooth at an approximate shooting distance of 300 mm. That is, an approximate error for a 10 mm tooth can be about 0.1 mm, yielding an error through photograph-constrained directions of approximately 0.3 mm. Embodiments are not limited to this particular example, which may generally illustrate the accuracy of one or more embodiments of the present disclosure.

Thus, the camera can be approximated with a composition of the projection π and a projective 2D to 2D transformation G. Having at least four points in the set P, action of G in homogenous coordinates is:

$$G(Y_i) = \begin{pmatrix} g_{11} & g_{12} & g_{13} \\ g_{21} & g_{22} & g_{23} \\ g_{31} & g_{32} & g_{33} \end{pmatrix} \cdot (Y_{i1} : Y_{i2} : 1)^T \qquad (2)$$

that is:

$$G(Y_i) = \left( \frac{g_{11}Y_{i1} + g_{12}Y_{i2} + g_{13}}{g_{31}Y_{i1} + g_{32}Y_{i2} + g_{33}}, \frac{g_{21}Y_{i1} + g_{22}Y_{i2} + g_{23}}{g_{31}Y_{i1} + g_{32}Y_{i2} + g_{33}} \right) \qquad (3)$$

in affine coordinates.

Coordinates of a point on the photograph 650 can be denoted as $(x_{i1}, x_{i2})$. Conditions $\{G(Y_i) = x_i\}$ for $1 \le i \le k$ can lead to an overdetermined system on G:

$$\begin{pmatrix} Y_{11} & Y_{12} & 1 & 0 & 0 & 0 & -x_{11}Y_{11} & -x_{11}Y_{12} & -x_{11} \\ 0 & 0 & 0 & Y_{11} & Y_{12} & 1 & -x_{12}Y_{11} & -x_{12}Y_{12} & -x_{12} \\ Y_{21} & Y_{22} & 1 & 0 & 0 & 0 & -x_{21}Y_{21} & -x_{21}Y_{22} & -x_{21} \\ 0 & 0 & 0 & Y_{21} & Y_{22} & 1 & -x_{22}Y_{21} & -x_{22}Y_{22} & -x_{22} \\ \vdots & \vdots & \vdots & \vdots & \vdots & \vdots & \vdots & \vdots & \vdots \\ Y_{k1} & Y_{k2} & 1 & 0 & 0 & 0 & -x_{k1}Y_{k1} & -x_{k1}Y_{k2} & -x_{k1} \\ 0 & 0 & 0 & Y_{k1} & Y_{k2} & 1 & -x_{k2}Y_{k1} & -x_{k2}Y_{k2} & -x_{k2} \end{pmatrix} \cdot \begin{pmatrix} g_{11} \\ g_{12} \\ g_{13} \\ g_{21} \\ g_{22} \\ g_{23} \\ g_{31} \\ g_{32} \\ g_{33} \end{pmatrix} = 0 \qquad (4)$$

Transformation G can be defined by a non-zero solution of the overdetermined system on G. Transformation G can represent a camera projection of the plane p to the 2D space of the photo image. $G^{-1}$ can represent the inverse mapping.

The transformation $G^{-1}$ can map marked photograph points x to plane p. X points are shown in black in FIG. 6 and transformed points $G^{-1}(Q)$ are shown in white (e.g., as empty points). For example, "$G^{-1}(x)$ point" 660 can represent x point 652 from photograph 650 transformed onto the 3D digital dental model 651.

3D points $G^{-1}(Q)$ can be used as target points for the points $\pi(P)$ (e.g., in order to position the upper jaw 653 and the lower jaw 655 in a bite configuration). For k≥5 in general $G \cdot \pi(P) \neq Q$. A photo attraction force can be defined at a point X∈P as:

$$F(X) = -\text{const} \cdot (\pi(X) - G^{-1}(x)) \quad (5)$$

where X∈Q is the 2D point corresponding to X.

A "photo attraction force" can be a simulated force on the 3D digital dental model 651 to aid in moving a jaw (e.g., the upper jaw 653 and/or the lower jaw 655) to a position relative to the opposite jaw such that the 3D digital dental model 651 is bite set (e.g., in a bite configuration). The photo attraction force, for example, can be applied to an X point in a direction parallel to the plane p and toward a "$G^{-1}(x)$ point" (e.g., toward a point mapped to the 3D digital dental model from the photograph of the patient's teeth in a bite configuration).

Figure 7A:
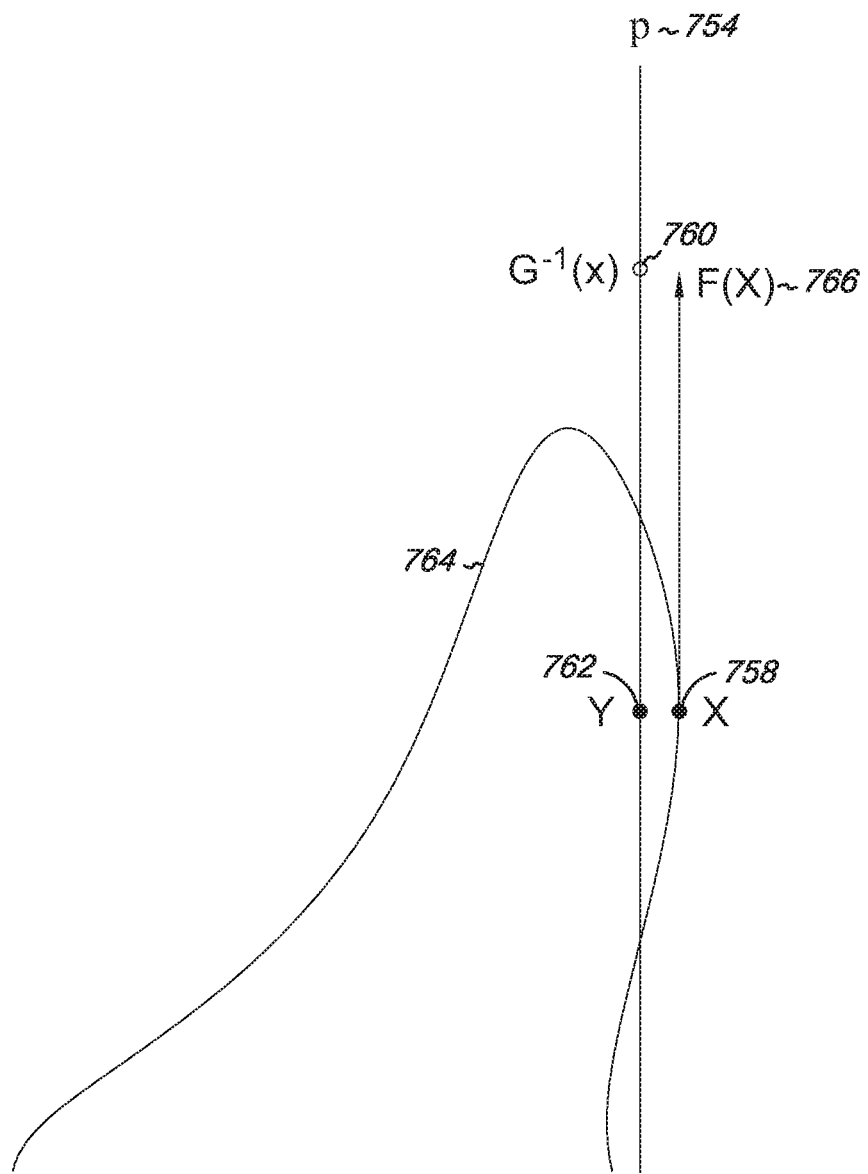
FIG. 7A illustrates a proximal view of a tooth from a digital dental model according to one or more embodiments of the present disclosure.

The transformed points can be targets of movement of 3D points Y∈π(P). Y points may generally be fairly close to X points, thus, for ease of illustration, Y points are not illustrated in FIG. 6. However, a Y point and an X point are illustrated in FIG. 7A.

Some embodiments can include the use of more than one photograph. In such embodiments, additional photographs can be taken of the patient's teeth from the same or different angles than the photograph 650 illustrated in FIG. 6. For example, embodiments can include the use of three photographs, one taken from the front of the patient's jaws (e.g., of the patient's anterior teeth), and one from each left and right sides of the patient's jaws (e.g., of the patient's left and posterior teeth respectively). However embodiments are not so limited, as a different number of photographs can be used with embodiments of the present disclosure.

In one or more embodiments, photographs of a patient's jaws can be taken from the same general perspective and include images of the patient's jaws in different relative positions (e.g., between opened and closed). Such embodiments can be beneficial in providing information suitable to ascertaining a range of motion of the patient's jaws and/or a pivot point for the patient's jaws. For example, a number of photographs can include the patient's jaws in an open configuration, in a closed configuration, and one or more positions between open and closed.

Points (e.g., x points) can be marked on a same position on the patient's jaws in each photograph. Corresponding X points can be marked on the 3D digital dental model 651. The X points can be fit to a common plane p as Y points. The x points can be mapped to the 3D digital dental model 651 to provide information regarding movement of the lower jaw 655. A pivot point of the lower jaw 655 can be extrapolated therefrom.

FIG. 7A illustrates a proximal view of a tooth from a 3D digital dental model according to one or more embodiments of the present disclosure. A tooth (e.g., tooth 764) can be one tooth in a digital dental model (e.g., digital dental model 651 illustrated in FIG. 6). As such, the tooth 764 can represent a tooth from a digital dental model that is not in a bite configuration.

The illustration of FIG. 7A can represent a transversal section of the sets P, $\pi(P)$, and $G^{-1}(Q)$ in that a point from each set is illustrated in association with the tooth 764. For example, the tooth 764 includes an X point 758, a Y point 762, and a point $G^{-1}(x)$ 760.

The X point 758 can be marked on the digital dental model by an operator in correspondence with an x point marked on a photograph of a patient's jaws. The Y point 762 can be a representation of the X point 758 projected onto plane p 754 in accordance with one or more embodiments of the present disclosure. As described herein, the plane p 754 can be fit to a number of X points marked on the digital dental model.

As the number of X points may not lie directly on the plane p 754, they may be projected onto the plane p 754 by a projection π as described herein. Such X points projected onto the plane p may be labeled as Y points. As the reader will appreciate, plane p 754 is illustrated in FIG. 7A as a line because it runs into and out of the page (e.g., the line illustrated in FIG. 7A as plane p 754 is a cross section of the plane p 754).

As illustrated in FIG. 7A, points mapped to a digital dental model from a photograph can be mapped to a plane p (e.g., a best-fit plane to a number of X points on the digital dental model). The $G^{-1}(Q)$ point (e.g., $G^{-1}(x)$ point 760) can represent an x point from a photograph mapped to the digital dental model associated with tooth 764. As used herein, mapping a point to a digital dental model can include mapping a point to 3D space associated with a digital dental model. For example, the point 760 has been mapped to space associated with the digital dental model of which the tooth 764 is a member, although the point 760 does not contact the tooth 764 as illustrated in FIG. 7A.

A photo attraction force (e.g., F(x) 766) can be applied to the digital dental model (e.g., to tooth 764) at an X point (e.g., X point 758). As illustrated in FIG. 7A, the photo attraction force can act parallel to the plane p 754. In some embodiments, the photo attraction force can act in the plane p, for example, when the X point lies in plane p.

Some embodiments can include simulating a number of photo attraction forces between X points (e.g., point 758) marked on the digital dental model corresponding to a number of x points marked on a photograph of a patent's jaws in a bite configuration and a number of $G^{-1}(x)$ points (e.g., point 760) mapped to the digital dental model from the number of x points marked on the photograph. In some instances, an X point and a Y point may be substantially proximate that a difference in effect on the digital dental model from simulating a force using the X point versus the Y point as an application point of the simulated force is negligible.

In various embodiments, when the digital dental model is allowed to move at least partially in response to the operation of the photo attraction force, a Y point associated with the X point to which the photo attraction force is applied can move towards a corresponding $G^{-1}(x)$ point. For example, as the photo attraction force F(X) 766 is applied to the X point 758, the Y point 762 can move toward the photograph mapped point $G^{-1}(x)$ 760. Accordingly, a jaw that is not held fixed in the digital dental model can move with the moving point. Such embodiments can be beneficial in helping to bite set a digital dental model using information obtained from one or more photographs of a patient's jaws in a bite configuration.

Figure 7B:
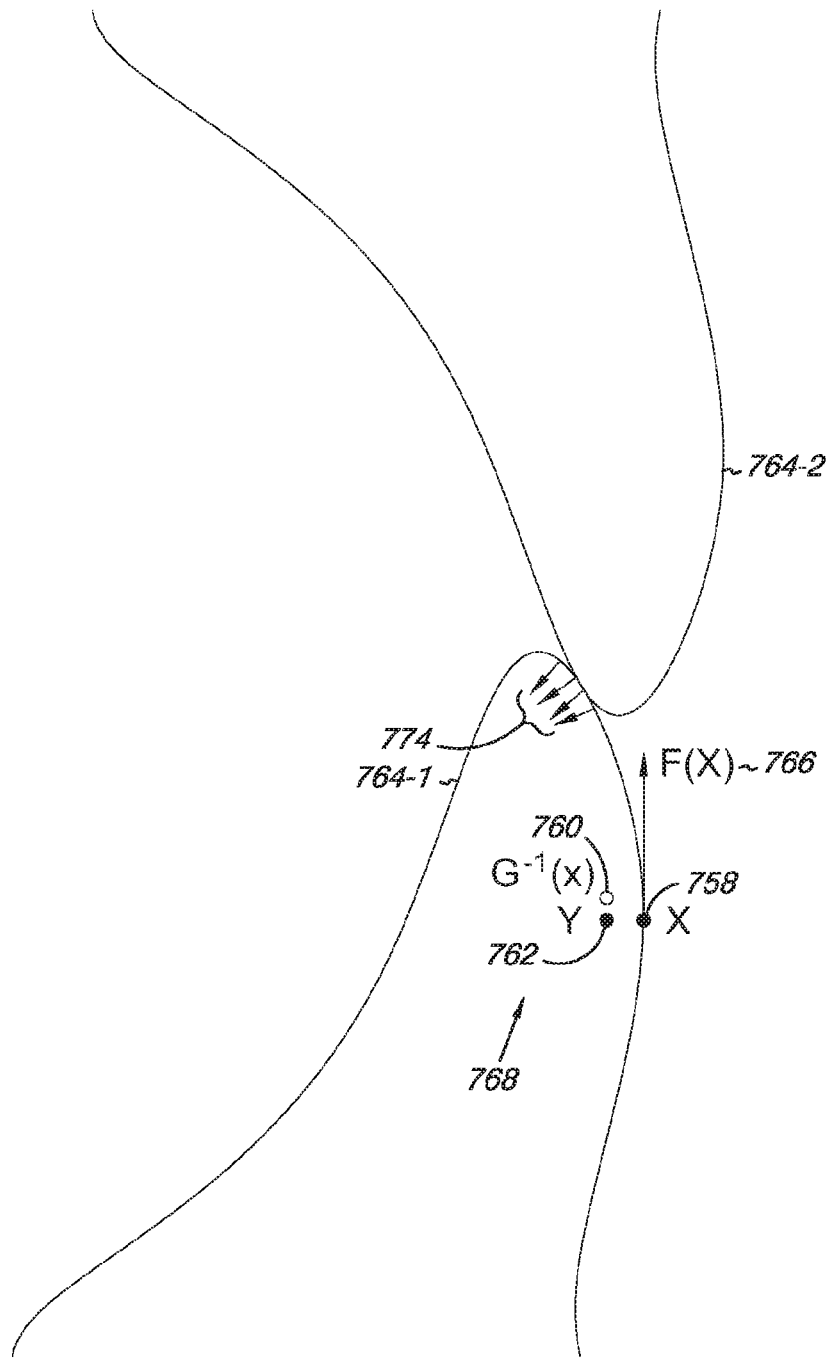
FIG. 7B illustrates a proximal view of the tooth from the digital dental model illustrated in FIG. 7A in a bite set position according to one or more embodiments of the present disclosure.

FIG. 7B illustrates a proximal view of the tooth from the digital dental model illustrated in FIG. 7A in a bite set position according to one or more embodiments of the present disclosure. The tooth 764-1 can be analogous to the tooth 764 in FIG. 7A. However, in FIG. 7B, the tooth 764-1 is in a bite set position with tooth 764-2.

In some embodiments, a bite set position can be reported for a digital dental model where an axial force, a number of photo attraction forces, and a number of reaction forces reach an equilibrium such that the jaw that is not fixed ceases moving in the simulation of movement of the digital dental model. A number of forces are illustrated acting on the tooth 764-1 such as an axial force 768, a photo attraction force 766, and a number of reaction forces 774.

The axial force 768 can be a force acting along an axis between an upper jaw and a lower jaw of a digital dental model. Although the axial force 768 illustrated in FIG. 7B reflects a force pointing upward from a lower jaw to an upper jaw, embodiments are not so limited. For example, an axial force can be applied to an upper jaw with respect to a lower jaw (e.g., a gravity force). In some embodiments, one jaw (e.g., either a lower jaw or an upper jaw) can be held fixed while a number of forces are applied to the opposite jaw.

In one or more embodiments, the axial force 768 can be applied at a center of mass of a jaw that is not held fixed in the digital dental model. In some embodiments, the axial force 768 can be applied at a center of mass of one or more teeth in a jaw that is not held fixed. As described herein, a jaw of the digital dental model can be segmented into a number of teeth (e.g., where each tooth is defined by a closed mesh).

The photo attraction force 766 illustrated in FIG. 7B can operate as described herein. With respect to the differences in the illustrations of FIGS. 7A and 7B, the tooth 764-1, and accordingly the remainder of the jaw associated therewith in the digital dental model, have moved to a bite set position. For example, tooth 764-1 has come into contact with tooth 764-2. As the Y point 762 associated with X point 758 has not reached its corresponding $G^{-1}(x)$ point, a photo attraction force 766 continues to be applied.

Likewise, Y point 762 has moved closer to $G^{-1}(x)$ point 760. In some instances, a bite set position may result where a Y point reaches a $G^{-1}(x)$ point. However, in other instances, a Y point may not reach a $G^{-1}(x)$ point, as illustrated in FIG. 7B. That is, the digital dental model may substantially cease moving due to the number of forces acting on the digital dental model reaching an equilibrium without all of the Y points on the digital dental model reaching their corresponding $G^{-1}(x)$ points (e.g., their targets of movement).

Due to contact between the tooth 764-1 and the tooth 764-2, a number of reaction forces 774 have been generated. As described herein, each tooth in a digital dental model can be represented by a closed mesh. The mesh can have any flat polygonal face. For example, the mesh can be triangular, and reaction forces can be calculated for each triangle of the mesh that lies within the contour of intersection of teeth that come into contact with each other. The reaction force for a particular triangle of the mesh that lies within the contour of intersection can be proportional to the area of the triangle and directed as a normal to the triangle. Embodiments are not limited to the use of triangular meshes for modeling teeth in the digital dental model as other types of meshes may be used.

Such reaction forces can help to prevent a first tooth from a first jaw of the digital dental model (e.g., tooth 764-1) from intersecting a second tooth (e.g., tooth 764-2) from a second jaw of the digital dental model. Such reaction forces can also aid in bite setting the digital dental model by aiding in determining a stable bite position. As one of ordinary skill in the art will appreciate, most dental patients may have only one stable bite position.

Figure 8A:
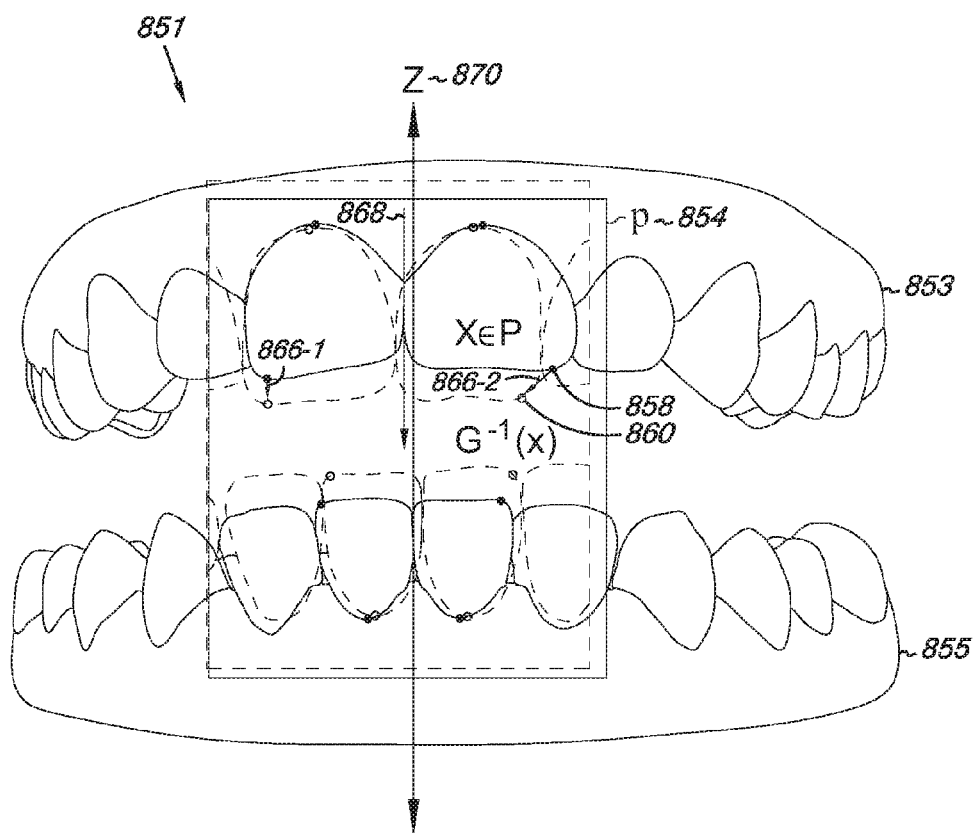
FIG. 8A illustrates a digital dental model in an initial position with a number of forces acting thereon according to one or more embodiments of the present disclosure.

FIG. 8A illustrates a digital dental model in an initial position with a number of forces acting thereon according to one or more embodiments of the present disclosure. The digital dental model 851 may be derived from an initial digital data set (IDDS) as described herein. The IDDS may be manipulated by a computing device having a graphical user interface (GUI) and software (e.g., executable instructions that can be executed by a processor to cause the computing device to perform operations, where the instructions can be stored on a computing device readable physical medium such as a magnetic disk, an optical disk, or a solid state semiconductor device, among others).

The digital dental model 851 may include a mesh (e.g., a triangular mesh). The mesh can be divided into a collection of closed meshes of separate teeth. Some embodiments can include modeling each tooth of the digital dental model 851 as a space volume with a constant density confined with a closed mesh.

As described herein, the digital dental model 851 can include an upper jaw 853 and a lower jaw 855 derived from scanning molds of a patient's upper jaw and lower jaw. Any scanning artifacts can be removed by appropriate algorithms or by a human operator. Likewise, a stomatological number can be assigned to each tooth of the model 851 by an algorithm or by an operator.

As a mold of a patient's upper jaw and a mold of a patient's lower jaw may be scanned separately, the upper jaw 853 and lower jaw 855 of the digital dental model 851 may have unique coordinate systems. Rigid movement $T_{final}$ can be found that transforms the coordinate system of the upper jaw 853 to the lower jaw 855, for example when the position of the lower jaw is fixed. However embodiments are not so limited, as the upper jaw 853 could be fixed while the lower jaw 855 could be allowed to move.

Once teeth are recognized on the digital dental model, an approximation of where the upper jaw 853 and lower jaw 855 should be located with respect to each other can be made. For example, an approximation can be made for where each tooth on the upper jaw 853 should be located with respect to a corresponding tooth on the lower jaw 855. Such an approximation is referred to herein as an initial position.

An initial position of the upper jaw 853 and lower jaw 855 of the digital dental model 851 can be formulated by fitting the two sets of corresponding 3D points by rigid transformation. Matching point clouds with given correspondence can be performed as will be appreciated by one of ordinary skill in the art.

From the initial position, the upper jaw 853 can be moved (e.g., "lifted") away from the lower jaw (e.g., in a direction along and/or parallel to the Z axis 870). For example, the upper jaw can be lifted approximately 10-15 mm. From this point, simulation of movement of the upper jaw 853 in response to a number of forces may commence. An initial position of the jaws of the digital dental model may be set before the simulation of movement.

The upper jaw 853 can move in response to an axial force 868 operating in the direction of the Z axis 870. The axial force 868 can act along an axis between a center of mass of the upper jaw 853 and a center of mass of the lower jaw 855. For example, the axial force 868 can be simulated as gravity.

The upper jaw 853 can also move in response to a number of photo attraction forces (e.g., photo attraction forces 866-1 and 866-2). When the upper jaw 853 comes into contact with the lower jaw 855, the upper jaw 853 can also move in response to a number of reaction forces (e.g., from a simulated collisions between one or more teeth of the upper jaw 853 and one or more teeth of the lower jaw 855).

Some embodiments include simulating movement of the upper jaw 853 in response to the axial force, the number of photo attraction forces, and the number of reaction forces simultaneously. In various embodiments, the axial force can be held constant (e.g., throughout the simulation of movement).

As illustrated in FIG. 8A, different photo attraction forces for different points can have different directions. For example, photo attraction force 866-1 acts in a different direction than photo attraction force 866-2 (e.g., between X point 858 and $G^{-1}(x)$ point 860). Some x points marked on a photograph and transformed onto plane p may not correspond exactly with X points marked on the digital dental model 851. That is, there may be some margin of error involved in marking corresponding points on both a photograph and on a digital dental model.

As described herein, jaws can be modeled as collections of separate teeth. Each tooth can be modeled as a space volume with a constant density (e.g., equal for all teeth), confined within a closed mesh (e.g., a triangular mesh). A reaction force can arise from each portion (e.g., triangle) of respective meshes of two or more teeth that intersect according to the simulation of movement. The reaction force can be proportional to the area of the mesh portion and directed as a normal to the mesh portion.

Simulation of movement may continue until the axial force and the number of photo attraction forces are compensated by the number of reaction forces. Such an equilibrium position (e.g., bite set) could be found, in some instances, without the use of photo attraction forces. However, in some instances, using an axial force and a number of reaction forces alone may yield an inaccurate and/or incorrect bite set.

For example, some malocclusions can constrain the freedom of movement of a jaw so that only part of the teeth, or fewer of the teeth, in the digital dental model have normal contact with teeth in the opposite jaw. In such instances, the upper jaw of the digital dental model may fall below its desired position during the simulation.

A similar problem can occur with digital dental models of patients who have one or more missing teeth. For example, if a patient has one or more missing molars on the lower jaw, simulation of movement of the upper jaw of the digital dental model can result in the upper jaw falling into the hole where the missing molar would be (e.g., under the action of the axial force).

Another example problem for digital dental modeling may occur for patients who have significant tooth inclination. When a tooth has significant deviation from its normal position in the dental arch (e.g., jaw) it can contact one or more teeth in the opposite jaw with the wrong lingual surface. Such an instance can lead to an erroneous bite set of the digital dental model without the use of photo attraction forces according to one or more embodiments of the present disclosure. That is, incorporating data from one or more photographs of the patient's jaws in a bite configuration can improve the accuracy of the bite setting process and reduce instances of erroneous bite setting due to patient tooth inclination, among other benefits.

An example scale of misalignment ($L_0$) of the bite set of the digital dental model due to such anomalies can be on the order of about 1 mm. In various embodiments, the forces applied to the digital dental model can be normalized such that: $F_{axial} \ll F_{photo}(L_0) \ll F_{reaction}(L_0)$ where $F_{axial}$ is the axial force (e.g., axial force 868), $F_{photo}(L_0)$ is the photo attraction force caused by a 3D misalignment of the size $L_0$, and $F_{reaction}(L_0)$ is the reaction force due to tooth intersection with a depth of $L_0$.

While simulation of movement and bite setting can be performed using classical mechanics, one or more embodiments of the present disclosure include the use of equations of energy-dissipating viscous movement. Such embodiments can provide better stability and convergence in the bite setting operation.

In various embodiments, simulation of movement of the digital dental model (e.g., of one jaw of the digital dental model) may be performed in discrete time steps. That is, the number of forces acting on the digital dental model may be calculated and applied for a discrete period of time, after which, the forces may be recalculated and reapplied. In some embodiments, the number of forces acting on the digital dental model (e.g., the axial force, the number of photo attraction forces, and/or the number of reaction forces) may be held constant during a particular time step.

During a bite setting operation, a first jaw of a digital dental model can be allowed to move while a second jaw of the digital dental model can be held fixed. Suppose that the origin of the first jaw coordinate system is at the center of mass of the first jaw. The position of the first jaw at time t can be defined by a transformation (R(t),T(t)), where R is a rotation component and T is a translation. Continuous motion equations are:

$$d/dt\ R = (1/\alpha)(\hat{I}^{-1}M)^x R \qquad (6)$$

$$d/dt\ T = (1/\alpha)(F/m) \qquad (7)$$

where:
I is the first jaw's inertia tensor with respect to rotations about the center of mass of the first jaw;
$\hat{I}$ is the inertia tensor transformed to a coordinate system of the second jaw;
$\alpha > 1$ is the viscosity constant;
m is the mass of the first jaw;
F is the total applied force; and
M is the total applied moment.

For any 3D vector V, the operator $V^x$ is defined by:

$$\begin{pmatrix} 0 & -V_3 & V_2 \\ V_3 & 0 & -V_1 \\ -V_2 & V_1 & 0 \end{pmatrix}. \qquad (8)$$

In some embodiments, the viscosity constant $\alpha$ and the time step of a numerical solution can be varied during simulation in order to reduce processing time.

Figure 8B:
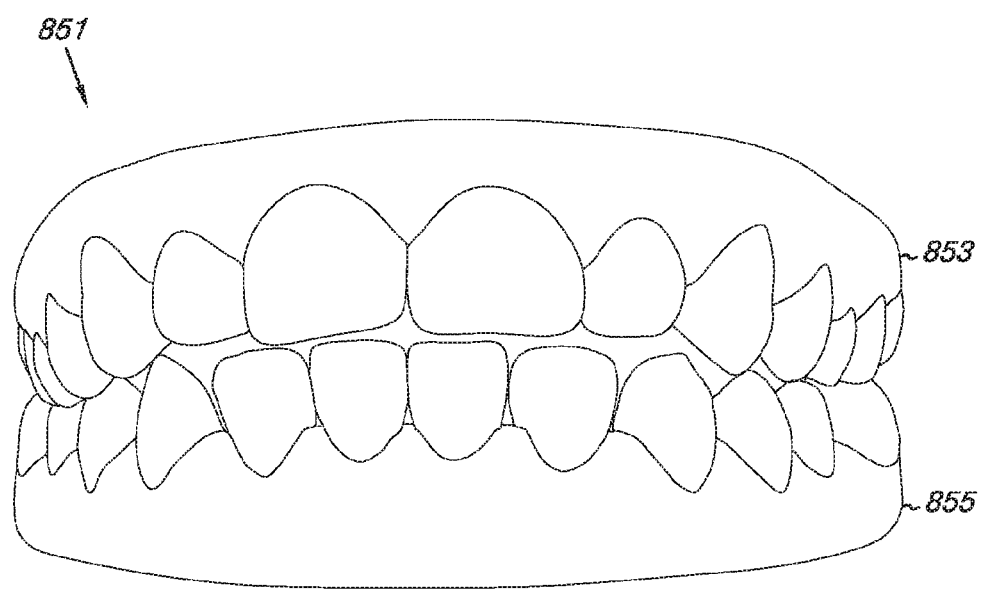
FIG. 8B illustrates the digital dental model of FIG. 8A in a bite set position according to one or more embodiments of the present disclosure.

FIG. 8B illustrates the digital dental model of FIG. 8A in a bite set position according to one or more embodiments of the present disclosure. The upper jaw 853 and the lower jaw 855 of the digital dental model 851, in the illustration of FIG. 8A, have reached a stable bite set position.

In some embodiments, a bite set can be reported when the axial force, the number of photo attraction forces, and the number of reaction forces reach an equilibrium. For example, the bite set can be reported when a jaw that is not fixed in the digital dental model (e.g., upper jaw 853) substantially ceases moving in the simulation of movement.

In some embodiments the simulation of movement can end when the non-fixed jaw remains in substantially the same position for at least two consecutive time steps. However, embodiments are not so limited as a different number of time steps can be selected.

Reporting a bite set can include providing a visual indication of a bite set for the digital dental model (e.g., in a bite configuration) on a display (e.g., on a computer monitor). The bite set can include the upper jaw 853 and the lower jaw 855 of the digital dental model 851 in a bite configuration. In various embodiments, reporting a bite set can include printing an image of the digital dental model 851 in a bite configuration (e.g., on a printing device coupled to a computing device).

Tests of an embodiment of the present disclosure have indicated that calculation of photo attraction forces (e.g., compared to simulation of movement with only an axial force and a number of reaction forces) does not hinder simulation of movement of a jaw of a digital dental model. An average computing device can provide convergence to a bite set in a matter of seconds. An additional benefit of one or more embodiments of the present disclosure includes the fact that an operator does not need to move the non-fixed jaw in six degrees of freedom in order for the bite setting operation to converge on an accurate solution, as may be the case with some previous approaches.

Figure 9:
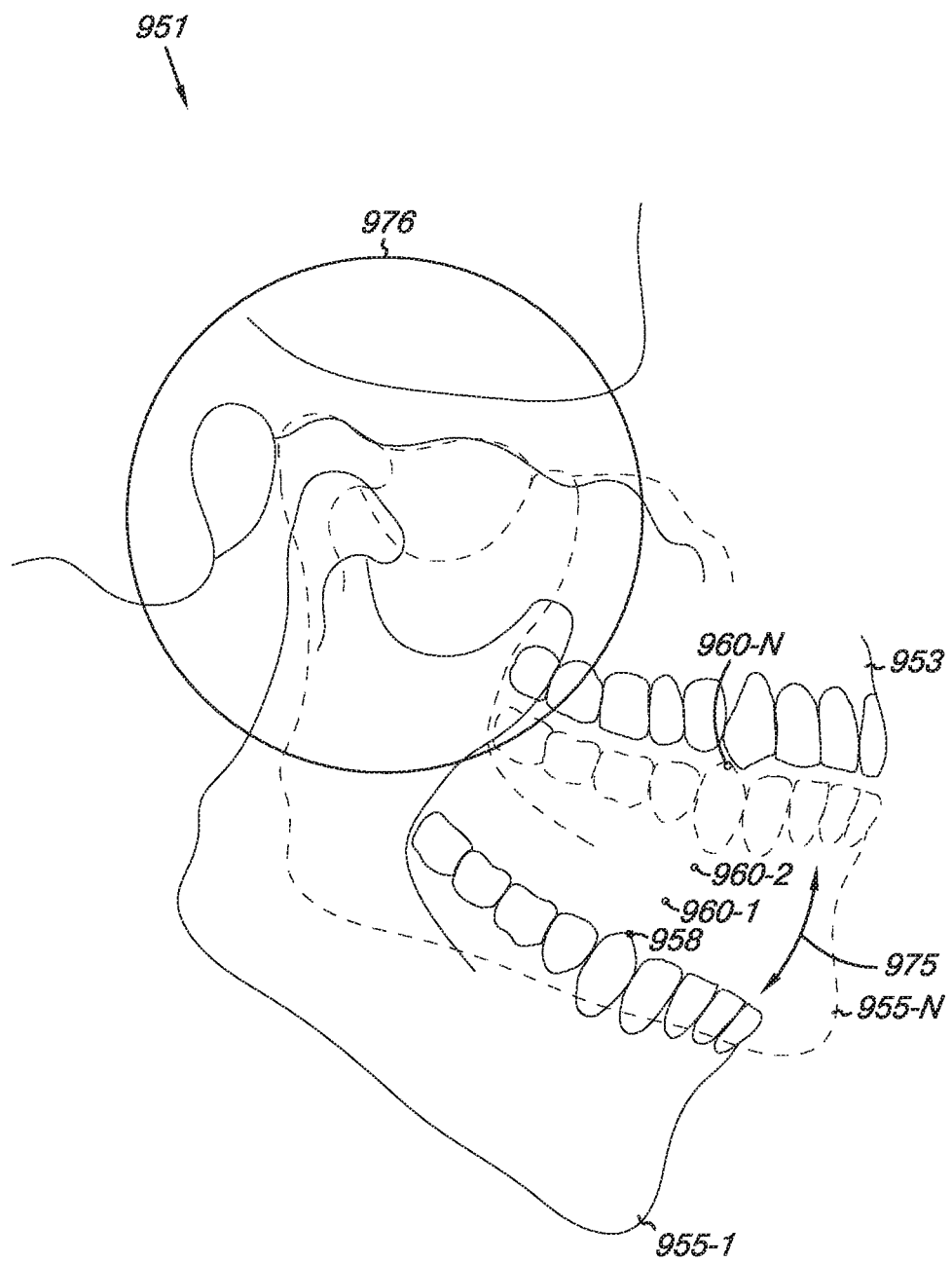
FIG. 9 illustrates a digital dental model with simulated anatomical movement of a lower jaw according to one or more embodiments of the present disclosure.

FIG. 9 illustrates a digital dental model with simulated anatomical movement of a lower jaw according to one or more embodiments of the present disclosure. The digital dental model 951 can include a simulation of anatomical movement 975 of the lower jaw 955-1, 955-N with respect to the upper jaw 953. The upper jaw 953 and lower jaw 955-1, 955-N can be part of a 3D data set, e.g., one or more IDDS.

With respect to FIG. 9, the solid outline of the lower jaw 955-1 represents the lower jaw in an open configuration with respect to the upper jaw 953. The dotted outline of the lower jaw 955-N represents the lower jaw in a closed configuration with respect to the upper jaw 953. The 3D digital dental model 951 can display the lower jaw in a number of configurations including opened, closed, as well as configurations therebetween.

An operator (e.g., a dental professional) can take a plurality of 2D images (e.g., photographs, X-rays, etc.) of at least a portion of a patient's jaws in a plurality of relative positions (e.g., opened, closed, and one or more different relative positions therebetween). The plurality of 2D images can comprise and/or provide data for a plurality of 2D data sets.

A plurality of 2D data sets, each derived from a 2D image of at least a portion of a patient's jaws can include a number of x points marked thereon, as described herein. A 2D data set can include a 2D image and/or points marked on the 2D image (e.g., using a GUI displaying the 2D image). Each 2D image of the patient's jaws can have corresponding x points marked thereon. For example, an x point marked on a tip of a mandibular lateral incisor can be marked on the tip of the mandibular lateral incisor in each 2D image to help provide consistency between 2D images for mapping to the 3D digital dental model.

The 3D digital dental model 351 can include a number of X points marked thereon (e.g., X point 958) corresponding to the x points marked on the plurality of 2D images. For each X point, a plurality of $G^{-1}(x)$ points (e.g., $G^{-1}(x)$ points 960-1, 960-2, ..., 960-N) can be mapped to the 3D digital dental model 951 as described herein. Although only one X point 958 and corresponding $G^{-1}(x)$ points 960-1, 960-2, ..., 960-N are illustrated in FIG. 9, embodiments are not so limited as a number of X points and corresponding $G^{-1}(x)$ points can be used.

In one or more embodiments, the plurality of $G^{-1}(x)$ points mapped to the 3D digital dental model for each X point can provide a basis for extrapolating a range of motion 975 for the lower jaw 955-1, 955-N with respect to the upper jaw 953. As described herein the plurality of $G^{-1}(x)$ points can be mapped to the 3D digital dental model by transforming a coordinate system of the 2D data to a coordinate system of the 3D data set.

Some embodiments can include determining a pivot point 976 (e.g., tempromandibular joint or TMJ) for the lower jaw 955-1, 955-N in the 3D digital dental model 951. For example, coordinates for a number of $G^{-1}(x)$ points (e.g., $G^{-1}(x)$ points 960-1, 960-2, ..., 960-N) associated with a first tooth and with a number of 2D images can be used to determine a focus of an arc created by the $G^{-1}(x)$ points. Embodiments are not limited to using this method for determining the pivot point of the lower jaw.

Figure 10:
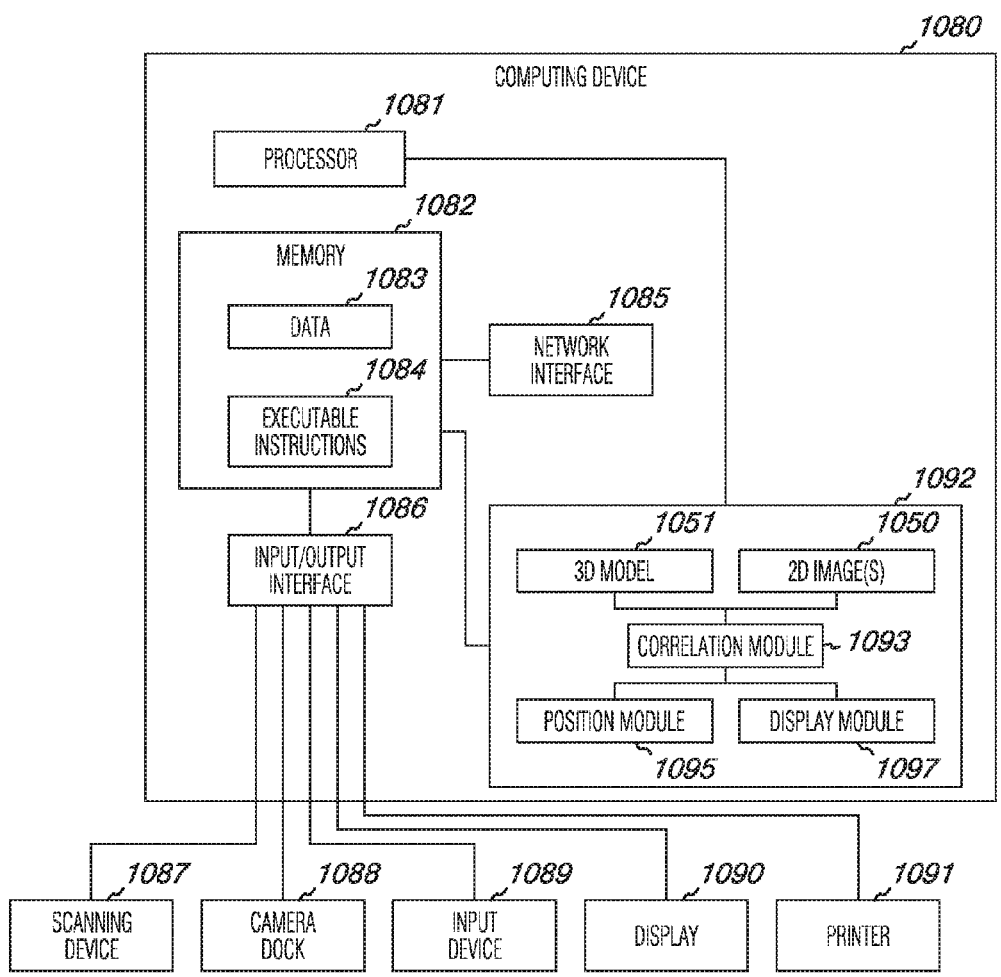
FIG. 10 illustrates a system for digital dental modeling according to one or more embodiments of the present disclosure.

FIG. 10 illustrates a system for digital dental modeling according to one or more embodiments of the present disclosure. In the system illustrated in FIG. 10, the system includes a computing device 1080 having a number of components coupled thereto. The computing device 1080 includes a processor 1081 and memory 1082. The memory can include various types of information including data 1083 and executable instructions 1084 as discussed herein.

Memory and/or the processor may be located on the computing device 1080 or off the device in some embodiments. As such, as illustrated in the embodiment of FIG. 10, a system can include a network interface 1085. Such an interface can allow for processing on another networked computing device or such devices can be used to obtain information about the patient or executable instructions for use with various embodiments provided herein.

As illustrated in the embodiment of FIG. 10, a system can include one or more input and/or output interfaces 1086. Such interfaces can be used to connect the computing device with one or more input or output devices.

For example, in the embodiment illustrated in FIG. 10, the system includes connectivity to a scanning device 1087, a camera dock 1088, an input device 1089 (e.g., a keyboard, mouse, etc.), a display device 1090 (e.g., a monitor), and a printer 1091. The input/output interface 1086 can receive data, storable in the data storage device (e.g., memory 1082), representing the digital dental model corresponding to the patient's upper jaw and the patient's lower jaw.

In some embodiments, the scanning device 1087 can be configured to scan a physical mold of a patient's upper jaw and a physical mold of a patient's lower jaw. In one or more embodiments, the scanning device 1087 can be configured to scan the patient's upper and/or lower jaws directly. The scanning device can be configured to input data to the correlation module 1093.

The camera dock 1088 can receive an input from an imaging device (e.g., a 2D imaging device) such as a digital camera or a printed photograph scanner. The input from the imaging device can be stored in the data storage device 1082. The input from the imaging device can represent a photograph, for example, of a patient's upper jaw and the patient's lower jaw in a bite configuration. The input from the imaging device can include data representing a point marked on the photograph.

The processor 1081 can be configured to provide a visual indication of a photograph and/or a digital dental model on the display 1090 (e.g., on a GUI running on the processor 1081 and visible on the display 1090). The GUI can be configured to allow a user to mark one or more points on the photograph and/or the digital dental model. Such points marked via the GUI can be received by the processor 1081 as data and/or stored in memory 1082. The processor 1081 can be configured to map points marked on the photograph to the digital dental model and to provide a visual indication of one or both on the display 1090.

Such connectivity can allow for the input and/or output of image information (e.g., scanned images or digital pictures, etc.) or instructions (e.g., input via keyboard) among other types of information. Although some embodiments may be distributed among various computing devices within one or more networks, such systems as illustrated in FIG. 10 can be beneficial in allowing for the capture, calculation, and/or analysis of information discussed herein.

The processor 1081, in association with the data storage device 1082, can be associated with data and/or application modules 1092. The processor 1081, in association with the data storage device 1082, can store and/or utilize data and/or execute instructions to provide a number of application modules for digital dental modeling.

Such data can include the 3D digital dental model 1051 described herein (e.g., including a first jaw and a second jaw) and a number of 2D images 1050 (e.g., of a patient's jaws corresponding to the jaws of the 3D digital dental model 1051). Such application modules can include a correlation module 1093, a position module 1095, and/or a display module 1097.

The correlation module 1093 can be configured to correlate one or more 2D images 1050 with the 3D digital dental model 1051. For example, the correlation module 1093 can be configured to transform points marked on the one or more 2D images 1050 from a coordinate system associated therewith to a coordinate system associated with the 3D digital dental model 1051.

The position module 1095 can be associated with the correlation module 1093 and configured to bite set the first jaw and the second jaw of the digital dental model based on output of the correlation module 1093. That is, the position module 1095 can provide the relative positioning and movement simulation of jaws of the 3D digital dental model described herein. In one or more embodiments, during a bite setting operation, the position module 1095 can be configured to use points marked on the 2D image and transformed from 2D to 3D coordinate systems as targets of movement for corresponding points marked on the 3D digital dental model.

According to one or more embodiments, the position module 1095 can be configured to simulate of anatomical movement of a lower jaw with respect to an upper jaw of the digital dental model based on an output of the correlation module 1093. For example, such output of the correlation module can include transformations of points marked on a plurality of 2D images from a coordinate system associated therewith to a coordinate system associated with the 3D digital dental model. The position module can be configured to determine a pivot point on the 3D digital dental model for the lower jaw and/or to extrapolate a range of motion of the lower jaw with respect to the upper jaw of the 3D digital dental model as described herein.

The display module 1097 can be associated with the correlation module 1093 and the position module 1095. The display module 1097 can be configured to provide a display of the 3D digital dental model and/or the 2D image of the patient's jaws. For example, the display module can provide a display of a simulation of anatomical movement output from the position module 1095. The display module 1097 can provide such a display via display 1090.

Functionality of the display module 1097 (e.g., via a GUI) can allow a user to mark points on the 2D image and corresponding points on the 3D digital dental model. The correspondence of points marked on the 2D image and the 3D digital dental model can be improved (e.g., deviation between corresponding points can be reduced) according to embodiments in which the display module 1097 provides a simultaneous display of the 2D image and the 3D digital dental model.

Although specific embodiments have been illustrated and described herein, those of ordinary skill in the art will appreciate that any arrangement calculated to achieve the same techniques can be substituted for the specific embodiments shown. This disclosure is intended to cover any and all adaptations or variations of various embodiments of the disclosure.

It is to be understood that the use of the terms "a", "an", "one or more", "a number of", or "at least one" are all to be interpreted as meaning one or more of an item is present. Additionally, it is to be understood that the above description has been made in an illustrative fashion, and not a restrictive one. Combination of the above embodiments, and other embodiments not specifically described herein will be apparent to those of skill in the art upon reviewing the above description.

It will be understood that when an element is referred to as being "on," "connected to" or "coupled with" another element, it can be directly on, connected, or coupled with the other element or intervening elements may be present. In contrast, when an element is referred to as being "directly on," "directly connected to" or "directly coupled with" another element, there are no intervening elements or layers present. As used herein, the term "and/or" includes any and all combinations of one or more of the associated listed items.

It will be understood that, although the terms first, second, etc. may be used herein to describe various elements and that these elements should not be limited by these terms. These terms are only used to distinguish one element from another element. Thus, a first element could be termed a second element without departing from the teachings of the present disclosure.

The scope of the various embodiments of the disclosure includes any other applications in which the above structures and methods are used. Therefore, the scope of various embodiments of the disclosure should be determined with reference to the appended claims, along with the full range of equivalents to which such claims are entitled.

In the foregoing Detailed Description, various features are grouped together in a single embodiment for the purpose of streamlining the disclosure. This method of disclosure is not to be interpreted as reflecting an intention that the embodiments of the disclosure require more features than are expressly recited in each claim.

Rather, as the following claims reflect, inventive subject matter lies in less than all features of a single disclosed embodiment. Thus, the following claims are hereby incorporated into the Detailed Description, with each claim standing on its own as a separate embodiment.

What is claimed:
1. A method for digital dental modeling, comprising:
receiving a three-dimensional data set including an upper jaw and a lower jaw of a three-dimensional digital dental model;

receiving a plurality of two-dimensional data sets each corresponding to at least a portion of the upper jaw and the lower jaw;

mapping two-dimensional data of the plurality of two-dimensional data sets to the three-dimensional digital dental model by transforming a coordinate system of the two-dimensional data to a coordinate system of the three-dimensional data set; and simulating anatomical movement of the lower jaw with respect to the upper jaw based on the two-dimensional data mapped to the three-dimensional data set in the three-dimensional digital dental model in response to applying simulated forces to the lower jaw including an axial force, a number of photo attraction forces, and a number of reaction forces from interaction of the upper jaw and the lower jaw.

2. The method of claim 1, wherein the method includes determining a pivot point for the lower jaw in the three-dimensional digital dental model.

3. The method of claim 1, wherein the method includes determining a range of motion for the lower jaw in the three-dimensional digital dental model.

4. The method of claim 1, wherein the method includes receiving a first portion of each of the plurality of two-dimensional data sets from a two-dimensional imaging device, where the first portion of each the plurality of two-dimensional data sets comprises one of a plurality of two-dimensional images, each of the plurality of two-dimensional images corresponding to the portion of the upper jaw and the lower jaw in different relative positions.

5. The method of claim 4, wherein the method includes receiving a second portion of each of the plurality of two-dimensional data sets from a graphical user interface displaying one of the plurality of two-dimensional images, where the second portion of each of the plurality of two-dimensional data sets comprises at least three points marked on one of the plurality of two-dimensional images.

6. The method of claim 1, wherein the method includes two-dimensionally imaging a patient's upper jaw and lower jaw in a plurality of relative positions to generate the plurality of two-dimensional data sets.

7. The method of claim 6, wherein the method includes two-dimensionally imaging the patient's upper jaw and lower jaw with one two-dimensional imaging device and without applying physical targets to the patient.

8. A system for digital dental modeling, comprising:
a three-dimensional digital dental model including an upper jaw and a lower jaw;
a plurality of two-dimensional images of a patient's upper jaw and lower jaw corresponding to the upper jaw and the lower jaw of the three-dimensional digital dental model;
a correlation module configured to correlate the plurality of two-dimensional images with the three-dimensional digital dental model; and
a position module associated with the correlation module and configured to simulate anatomical movement of the lower jaw with respect to the upper jaw of the three-dimensional digital dental model in response to applying simulated forces to the lower jaw including an axial force, a number of photo attraction forces, and a number of reaction forces from interaction of the upper jaw and the lower jaw.

9. The system of claim 8, wherein the simulated anatomical movement of the lower jaw is based on an output of the correlation module.

10. The system of claim 8, wherein the system includes a display module associated with the position module and configured to provide a display of the anatomical movement output from the position module.

11. The system of claim 8, wherein the plurality of two-dimensional images depict the patient's upper jaw and lower jaw in a plurality of different positions between opened and closed.

12. The system of claim 8, wherein the position module is configured to extrapolate a range of motion of the lower jaw with respect to the upper jaw.

13. The system of claim 8, wherein the position module is configured to determine a pivot point on the three-dimensional digital dental model for the lower jaw.

14. The system of claim 8, wherein the system includes one two-dimensional imaging device configured to generate the plurality of two-dimensional images without artificial targets applied to the patient and without predetermined positioning of the two-dimensional imaging device.

15. A non-transitory computing device readable medium storing a set of instructions executable to cause the computing device to:
map two-dimensional data of a plurality of two-dimensional data sets each corresponding to at least a portion of an upper jaw and a lower jaw to a three-dimensional digital dental model including the upper jaw and the lower jaw by transforming a coordinate system of the two-dimensional data to a coordinate system of the three-dimensional data set; and
simulate anatomical movement of the lower jaw with respect to the upper jaw based on the two-dimensional data mapped to the three-dimensional data set in the three-dimensional digital dental model in response to applying simulated forces to the lower jaw including an axial force, a number of photo attraction forces, and a number of reaction forces from interaction of the upper jaw and the lower jaw.

16. The medium of claim 15, including instructions to determine a pivot point for the lower jaw in the three-dimensional digital dental model.

17. The medium of claim 15, including instructions to determine a range of motion for the lower jaw in the three-dimensional digital dental model.

18. The medium of claim 15, wherein a first portion of each of the plurality of two-dimensional data sets originated from a two-dimensional imaging device,
where the first portion of each the plurality of two-dimensional data sets comprises one of a plurality of two-dimensional images, and
where each of the plurality of two-dimensional images corresponding to the portion of the upper jaw and the lower jaw in different relative positions.

19. The medium of claim 18, including instructions to display one of the plurality of two dimensional images on a graphical user interface.

20. The medium of claim 19, including instructions to receive input from a user, comprising at least three points marked on the one of the plurality of two-dimensional images, via the graphical user interface, as a second portion of each of the plurality of two-dimensional data sets.

* * * * *